(12) United States Patent
Kim et al.

(10) Patent No.: US 9,918,937 B2
(45) Date of Patent: Mar. 20, 2018

(54) PHARMACEUTICAL COMPOSITION FOR PROTECTING WOUNDS, PROVIDING HEMOSTASIS, OR PREVENTING ADHESION IN THE GASTROINTESTINAL TRACT

(71) Applicants: DAEWOONG CO., LTD., Seongnam-si, Gyeonggi-do (KR); CG BIO CO., LTD., Seongnam-si, Gyeonggi-do (KR); UTAH-INHA DDS & ADVANCED THERAPEUTICS RESEARCH CENTER, Incheon (KR)

(72) Inventors: In-Ae Kim, Seoul (KR); Sang-Hee Kim, Gwacheon-si (KR); Ji-Hoon Jung, Yongin-si (KR); Hee-Chul Chang, Seoul (KR); Jin-Hee Maeng, Bucheon-si (KR); Su-Geun Yang, Incheon (KR); Don-Haeng Lee, Seoul (KR); Kyung-Hyun Min, Yongin-si (KR)

(73) Assignees: DAEWOONG CO., LTD., Seongnam-si, Gyeonggi-do (KR); CG BIO CO., LTD., Seongnam-si, Gyeonggi-do (KR); UTAH-INHA DDS & ADVANCED THERAPEUTICS RESEARCH CENTER, Incheon (KR)

( * ) Notice: Subject to any disclaimer, the term of this patent is extended or adjusted under 35 U.S.C. 154(b) by 0 days.

(21) Appl. No.: 14/763,335

(22) PCT Filed: Oct. 31, 2013

(86) PCT No.: PCT/KR2013/009783
§ 371 (c)(1),
(2) Date: Jul. 24, 2015

(87) PCT Pub. No.: WO2014/119836
PCT Pub. Date: Aug. 7, 2014

(65) Prior Publication Data
US 2015/0352049 A1   Dec. 10, 2015

(30) Foreign Application Priority Data

Jan. 30, 2013  (KR) .................... 10-2013-0010579

(51) Int. Cl.
| | | |
|---|---|---|
| A61K 9/00 | (2006.01) |
| A61K 33/00 | (2006.01) |
| A61K 38/00 | (2006.01) |
| A61K 9/14 | (2006.01) |
| A61K 33/14 | (2006.01) |
| A61K 38/18 | (2006.01) |
| A61K 47/38 | (2006.01) |
| A61K 47/10 | (2017.01) |
| A61K 47/32 | (2006.01) |
| A61K 47/36 | (2006.01) |
| A61L 31/04 | (2006.01) |
| A61L 31/14 | (2006.01) |
| A61L 31/16 | (2006.01) |
| A61L 24/00 | (2006.01) |
| A61L 24/04 | (2006.01) |

(52) U.S. Cl.
CPC ............ *A61K 9/146* (2013.01); *A61K 9/0053* (2013.01); *A61K 9/0095* (2013.01); *A61K 33/14* (2013.01); *A61K 38/18* (2013.01); *A61K 38/1808* (2013.01); *A61K 47/10* (2013.01); *A61K 47/32* (2013.01); *A61K 47/36* (2013.01); *A61K 47/38* (2013.01); *A61L 24/0015* (2013.01); *A61L 24/0031* (2013.01); *A61L 24/043* (2013.01); *A61L 31/041* (2013.01); *A61L 31/145* (2013.01); *A61L 31/16* (2013.01); *A61K 2300/00* (2013.01); *A61L 2300/414* (2013.01); *A61L 2400/04* (2013.01); *A61L 2400/06* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,588,762 A * | 5/1986 | Mruk | ............. | A61B 5/0408 156/327 |
| 4,717,717 A * | 1/1988 | Finkenaur | ............ | A61K 9/0048 514/7.6 |
| 5,578,661 A * | 11/1996 | Fox | ............. | A61L 15/225 514/944 |
| 5,662,924 A * | 9/1997 | Rhodes | ............. | A61L 15/28 424/445 |
| 6,248,363 B1 * | 6/2001 | Patel | ............. | A61K 9/1617 424/422 |
| 6,960,617 B2 * | 11/2005 | Omidian | ............. | A61K 9/0065 521/102 |
| 7,674,480 B2 * | 3/2010 | Fleshner-Barak | ... | A61K 9/0065 424/486 |
| 7,776,345 B2 * | 8/2010 | Dudhara | ............. | A61K 9/0007 424/400 |

(Continued)

FOREIGN PATENT DOCUMENTS

| | | |
|---|---|---|
| JP | 2012-72061 A | 4/2012 |
| KR | 10-0320771 B1 | 1/2002 |
| WO | 2006/049463 A1 | 5/2006 |

OTHER PUBLICATIONS

Arza et al., AAPS PharmSciTech, 2009, 10(1):220-226.*
Omidian et al. J. Drug Del. Sci. Tech., 2008; 18(2):83-93.*

*Primary Examiner* — Robert A Wax
*Assistant Examiner* — Olga V Tcherkasskaya
(74) *Attorney, Agent, or Firm* — Vorys, Sater, Seymour & Pease LLP; Mih Suhn Koh (57) ABSTRACT

The present invention provides a pharmaceutical composition in a powder form for providing wound protection, hemostasis, or anti-adhesion in the gastrointestinal tract, which comprises a certain mucoadhesive polymer; and a certain hygroscopic agent.

13 Claims, 11 Drawing Sheets

(56) References Cited

U.S. PATENT DOCUMENTS

| | | | |
|---|---|---|---|
| 8,673,333 B2* | 3/2014 | Elisseeff | A61K 9/06 424/423 |
| 8,846,105 B2* | 9/2014 | Koopman | A61K 9/12 424/499 |
| 2002/0015731 A1* | 2/2002 | Appel | A61K 9/0004 424/473 |
| 2003/0086972 A1* | 5/2003 | Appel | A61K 9/0004 424/473 |
| 2004/0162263 A1* | 8/2004 | Sands | A61K 9/2846 514/46 |
| 2005/0147690 A1* | 7/2005 | Masters | A61K 9/1658 424/499 |
| 2005/0202090 A1* | 9/2005 | Clarke | A61J 3/10 424/486 |
| 2007/0059350 A1* | 3/2007 | Kennedy | A61F 13/00068 424/448 |
| 2010/0209495 A1* | 8/2010 | Li | A61K 9/2018 424/452 |
| 2011/0097401 A1* | 4/2011 | Phillips | A61K 9/0053 424/479 |
| 2012/0301436 A1* | 11/2012 | Yang | A61K 9/0024 424/93.7 |

* cited by examiner

A: Non-treated group
B: Formulation-treated group
C: Epinephrine-treated group

A: Non-treated group
B: Formulation-treated group

PHARMACEUTICAL COMPOSITION FOR PROTECTING WOUNDS, PROVIDING HEMOSTASIS, OR PREVENTING ADHESION IN THE GASTROINTESTINAL TRACT

CROSS-REFERENCE TO RELATED APPLICATIONS

This application is a 371 of PCT/KR2013/009783, filed Oct. 31, 2013, which claims the benefit of Korean Patent Application No. 10-2013-0010579, filed Jan. 30, 2013. The content of these applications are incorporated by reference in their entirety into the instant application.

TECHNICAL FIELD

The present invention relates to a pharmaceutical composition for providing wound protection, hemostasis, or anti-adhesion in the gastrointestinal tract. More specifically, the present invention relates to a pharmaceutical composition in a powder form for providing wound protection, hemostasis, or anti-adhesion in the gastrointestinal tract, which comprises a certain mucoadhesive polymer; and a certain hygroscopic agent.

BACKGROUND ART

Gastrointestinal bleeding is a fairly common medical problem. About 50% of patients suffering from gastric ulcer are diagnosed as hemorrhagic gastric ulcer. In about 80% of the cases, gastrointestinal bleeding mostly occurs in the upper-gastrointestinal tract. In upper-gastrointestinal bleeding, the bleeding originates in the esophagus, stomach, or duodenum, and results in haematemesis and *melaena*. A bleeding site in upper-gastrointestinal bleeding can be identified by an endoscopic method; and the identification rate thereof is about 90%. Gastric or colonic polypectromies, endoscopic mucosal resections, and endoscopic treatments are variously performed in order to treat gastric or colon cancer. However, during or after such treatments, sometimes bleeding from the stomach or colon occurs, which may require emergency surgical interventions or even lead to death of the patient.

Recently, endoscopic hemostatic methods are being performed in order to treat gastrointestinal bleeding. The endoscopic hemostatic methods include, for example, a direct local-injection of hypertonic saline, epinephrine, or alcohol; a coagulation therapy using electric heat, argon or laser; and a physical hemostatic method using a clip. However, the conventional methods aim at reducing the amount of bleeding, through pressing by injecting a liquid agent into blood vessels around an ulcer or through ligating blood vessels per se. Accordingly, the ulcer remains as its mucous membrane is exfoliated. As a result, even after the treatment, the bleeding often continues. According to research studies, the conventional endoscopic hemostatic treatment is successful in only 70 to 80% of the cases. Further, bleeding reoccurs in 20 to 25% of the cases, 3 to 4 days after the endoscopic hemostatic treatment. Re-bleeding refers to bleeding from a blood vessel, and occurs before the ulcer is completely cured by the regeneration of tissue around the ulcer. Thus, there are limitations difficult to be solved by the conventional endoscopic hemostatic methods that stop bleeding when the mucous membrane of the ulcer is exfoliated. That is, in the conventional endoscopic hemostatic methods, healing rate of the ulcer or the lesion is too slow and re-bleeding frequently occurs. In order to solve the problems, the Korean patent publication no. 10-2006-0040329 has disclosed a hemostatic agent for internal body use and a method of applying the hemostatic agent onto an ulcer inside the human body, in which a coating agent having a polymer-solution form is dispersed and coated onto the ulcer in an endoscopic manner to stop bleeding from the ulcer and minimize the possibility of re-bleeding.

Meanwhile, in order to increase the healing rate of the ulcer or the lesion and minimize the possibility of re-bleeding, a multi-functional formulation that can effectively protect wounds (e.g., ulcer and/or lesion) and prevent adhesion, as well as stop bleeding (i.e., providing hemostasis), is required. That is, there is required a formulation administered (or injected) into the gastrointestinal tract through an endoscopic catheter, thereby protecting wounds, providing hemostasis, and/or preventing adhesion. In order to perform local administration into the gastrointestinal tract, the formulation requires not only having an appropriate viscosity and mucosal adhesiveness (i.e., mucoadhesiveness), but also forming a physical protective shield for providing hemostasis in a target area.

For preventing adhesion in an operational region, formulations having a gel form or a sol-gel form have been developed. However, gel formulations having low-viscosity involve many losses thereof during the application to the upper gastrointestinal tract, which results in restricted formation of the physical protective shield. And, although gel formulations having high-viscosity have an excellent mucoadhesiveness, they have disadvantages, for example requiring a high-pressure ejecting device, involving many losses thereof, etc. Sol-gel formulations refer to a formulation changing from a sol form (e.g., before applying into the body) to a gel form at a certain temperature (e.g., body temperature). However, conventional sol-gel formulations have a very short gelation time, which may lead to forming a gel in a catheter before applying into the body; and still involve many losses thereof during the application.

DISCLOSURE

Technical Problem

The present inventors performed various researches for developing a pharmaceutical formulation administered (or injected) into the gastrointestinal tract through an endoscope, thereby protecting wounds, providing hemostasis, and/or preventing adhesion in the gastrointestinal tract. Surprisingly, it has been newly found by the present invention that the formulations having a powder form, which was obtained by the combinations of a certain mucoadhesive polymer and a certain hygroscopic agent, has an appropriate mobility (or fluidity) suitable for passing through a catheter and/or applying to the body; forms a shield through immediate gel-formation at the applied site so as to minimize any loss thereof; and provides rapid wound-protection, hemostasis, and anti-adhesion (i.e., preventing adhesion).

Therefore, it is an object of the present invention to provide a pharmaceutical composition in a powder form for providing wound protection, hemostasis, or anti-adhesion in the gastrointestinal tract, which comprises a certain mucoadhesive polymer and a certain hygroscopic agent.

Technical Solution

In accordance with an aspect of the present invention, there is provided a pharmaceutical composition in a powder form for providing wound protection, hemostasis, or anti-adhesion in the gastrointestinal tract, which comprises a mucoadhesive polymer selected from the group consisting of hydroxyethyl cellulose, polyethylene oxide, and a mixture thereof; and a hygroscopic agent selected from the group consisting of croscarmellose sodium, sodium starch glycolate, crospovidone, and a mixture thereof.

The pharmaceutical composition of the present invention may further comprise an inorganic material selected from the group consisting of calcium chloride, calcium phosphate, calcium hydroxide, calcium silicate, calcium sulfate, and a mixture thereof. Preferably, the pharmaceutical composition of the present invention may be for administering into the gastrointestinal tract through an endoscope.

In an embodiment, the mucoadhesive polymer and the hygroscopic agent may be present in an amount ranging from 70 to 95 wt/wt % and from 5 to 30 wt/wt %, based on the total weight of the composition, respectively.

In another embodiment, the mucoadhesive polymer, the hygroscopic agent, and the inorganic material may be present in an amount ranging from 40 to 75 wt/wt %, from 5 to 30 wt/wt %, and from 10 to 40 wt/wt %, based on the total weight of the composition, respectively. Preferably, the mucoadhesive polymer, the hygroscopic agent, and the inorganic material may be present in an amount ranging from 50 to 70 wt/wt %, from 10 to 20 wt/wt %, and from 10 to 30 wt/wt %, based on the total weight of the composition, respectively.

The pharmaceutical composition of the present invention may further comprise a wound-healing agent selected from the group consisting of epidermal growth factor, keratinocyte growth factor, basic fibroblast growth factor, and a mixture thereof; and preferably epidermal growth factor.

Advantageous Effects

The pharmaceutical composition according to the present invention has a powder form, which can avoid the problems associated in the conventional formulations of a solution, gel, or sol-gel form. That is, the pharmaceutical composition in a powder form according to the present invention has an appropriate mobility (or fluidity) suitable for passing through a catheter and/or applying to the body; forms a shield through immediate gel-formation at the applied site so as to minimize any loss thereof; and can provide rapid wound-protection, hemostasis, and anti-adhesion (i.e., preventing adhesion). Especially, the composition of the present invention providing immediate gel-formation shows more excellent hemostatic and anti-adhesive potential, in comparison with a conventional hemostatic formulation simply adsorbed to bleeding site.

BEST MODE

The present invention provides a pharmaceutical composition in a powder form for providing wound protection, hemostasis, or anti-adhesion in the gastrointestinal tract, which comprises a mucoadhesive polymer selected from the group consisting of hydroxyethyl cellulose, polyethylene oxide, and a mixture thereof; and a hygroscopic agent selected from the group consisting of croscarmellose sodium, sodium starch glycolate, crospovidone, and a mixture thereof.

As used herein, the term "powder form" comprises any and all powder forms, including, for example, a pharmaceutical powder form and a pharmaceutical granular form (i.e., granules) obtained through conventional formulation methods.

The present inventors evaluated various items including protective shield-forming ability by immediate gelation, gel strength and hemostatic potential, in regard to various combinations of mucoadhesive polymers and hygroscopic agents. Surprisingly, it has been newly found by the present invention that the formulations having a powder form, which was obtained by the combinations of a certain mucoadhesive polymer and a certain hygroscopic agent, has an appropriate mobility (or fluidity) suitable for passing through a catheter and/or applying to the body; forms a shield through immediate gel-formation at the applied site so as to minimize any loss thereof; and provides rapid wound-protection, hemostasis, and anti-adhesion (i.e., preventing adhesion).

The pharmaceutical composition of the present invention may be for administering into the gastrointestinal tract through an endoscope (i.e., endoscopic catheter).

In an embodiment, the pharmaceutical composition of the present invention may comprise a mucoadhesive polymer and a hygroscopic agent, in which the mucoadhesive polymer and the hygroscopic agent may be present in an amount ranging from 70 to 95 wt/wt % and from 5 to 30 wt/wt %, based on the total weight of the composition, respectively.

In another embodiment, the pharmaceutical composition of the present invention may comprise, in addition to a mucoadhesive polymer and the hygroscopic agent, an inorganic material selected from the group consisting of calcium chloride, calcium phosphate, calcium hydroxide, calcium silicate, calcium sulfate, and a mixture thereof. In this embodiment, the mucoadhesive polymer, the hygroscopic agent, and the inorganic material may be present in an amount ranging from 40 to 75 wt/wt %, from 5 to 30 wt/wt %, and from 10 to 40 wt/wt %, based on the total weight of the composition, respectively. Preferably, the mucoadhesive polymer, the hygroscopic agent, and the inorganic material may be present in an amount ranging from 50 to 70 wt/wt %, from 10 to 20 wt/wt %, and from 10 to 30 wt/wt %, based on the total weight of the composition, respectively.

The pharmaceutical composition of the present invention may further comprise a wound-healing agent for facilitating wounds (e.g., ulcers and/or lesions) in the gastrointestinal tract. For example, the pharmaceutical composition of the present invention may further comprise a wound-healing agent selected from the group consisting of epidermal growth factor, keratinocyte growth factor, basic fibroblast growth factor, and a mixture thereof; and preferably epidermal growth factor. The wound-healing agent may be used in a therapeutically effect amount, which may be easily determined by a person skilled in the art.

In an embodiment of the present invention, there is provided a pharmaceutical composition consisting of hydroxyethyl cellulose, croscarmellose sodium, and sodium starch glycolate. For example, the pharmaceutical composition of the present invention may consist of 90 wt/wt % of hydroxyethyl cellulose, 5 wt/wt % of croscarmellose sodium, and 5 wt/wt % of sodium starch glycolate. And also, the pharmaceutical composition of the present invention may consist of 85 wt/wt % of hydroxyethyl cellulose, 7.5 wt/wt % of croscarmellose sodium, and 7.5 wt/wt % of sodium starch glycolate.

In another embodiment of the present invention, there is provided a pharmaceutical composition consisting of hydroxyethyl cellulose, croscarmellose sodium, sodium starch glycolate, and epidermal growth factor. For example, the pharmaceutical composition of the present invention may consist of 89.99 wt/wt % of hydroxyethyl cellulose, 5 wt/wt % of croscarmellose sodium, 5 wt/wt % of sodium starch glycolate, and 0.01 wt/wt % of epidermal growth factor.

In still another embodiment of the present invention, there is provided a pharmaceutical composition consisting of hydroxyethyl cellulose and sodium starch glycolate. For example, the pharmaceutical composition of the present invention may consist of 90 wt/wt % of hydroxyethyl cellulose and 10 wt/wt % of sodium starch glycolate.

In still another embodiment of the present invention, there is provided a pharmaceutical composition consisting of hydroxyethyl cellulose, polyethylene oxide, sodium starch glycolate, and calcium chloride. For example, the pharmaceutical composition of the present invention may consist of 30 wt/wt % of hydroxyethyl cellulose, 20 wt/wt % of polyethylene oxide, 20 wt/wt % of sodium starch glycolate, and 30 wt/wt % of calcium chloride.

The present invention will be described in further detail with reference to the following examples. These examples are for illustrative purposes only and are not intended to limit the scope of the present invention.

Example 1: Preparation and Evaluation of Powder Formulations (1) Preparation of Powder Formulations Preliminary tests for mucosal adhesiveness were performed on various types of mucoadhesive polymer. And also, preliminary tests for hygroscopic capacity were performed on various hygroscopic agents. As the results of the preliminary tests, hydroxyethyl cellulose (HEC), sodium alginate, chitosan, hydroxypropyl cellulose (HPC), and polyethylene oxide (PEO) showed excellent mucosal adhesiveness; and croscarmellose sodium (Ac-di-sol), sodium starch glycolate, calcium silicate, and crospovidone showed very excellent hygroscopicity. From the results of the preliminary tests, the powder formulations shown in the following Table 1 were prepared by mixing the mucoadhesive polymer(s) and the hygroscopic agents, optionally along with a known hemostatic inorganic material (calcium chloride). The amounts of Table 1 represent the wt/wt % (percent by weight) in the formulation.

TABLE 1

| Sample | Mucoadhesive polymer | | | | | Hygroscopic agent | | | Inorganic material calcium chloride |
|---|---|---|---|---|---|---|---|---|---|
| | HEC | sodium alginate | chitosan | HPC | PEO | Ac-di-sol | sodium starch glycolate | crospovidone | |
| S1 | — | — | — | — | — | 50 | 50 | — | — |
| S2 | 90 | — | — | — | — | 5 | 5 | — | — |
| S2-1 | 85 | — | — | — | — | 7.5 | 7.5 | — | — |
| S2-2 | 80 | — | — | — | — | 10 | 10 | — | — |
| S2-3 | 75 | — | — | — | — | 12.5 | 12.5 | — | — |
| S2-4 | 70 | — | — | — | — | 15 | 15 | — | — |
| S2-5 | 65 | — | — | — | — | 17.5 | 17.5 | — | — |
| S2-6 | 60 | — | — | — | — | 20 | 20 | — | — |
| S2-7 | 90 | — | — | — | — | — | 10 | — | — |
| S2-8 | 85 | — | — | — | — | — | 15 | — | — |
| S3 | — | 33.3 | — | — | — | 33.3 | 33.3 | — | — |
| S4 | — | — | 33.3 | — | — | 33.3 | 33.3 | — | — |
| S5 | — | — | — | 33.3 | — | 33.3 | 33.3 | — | — |
| S6 | 30 | — | — | — | 20 | — | 20 | — | 30 |
| S6-1 | 50 | — | — | — | 20 | — | 20 | — | 10 |
| S6-2 | 30 | — | — | — | 45 | — | 20 | — | 5 |
| S6-3 | 30 | — | — | — | 20 | — | — | 20 | 30 |
| S7 | 40 | — | — | — | 20 | — | 10 | — | 30 |
| S8 | 30 | — | — | — | 20 | 10 | 10 | — | 30 |
| S8-1 | 45 | — | — | — | 20 | 10 | 10 | — | 15 |
| S8-2 | 30 | — | — | — | 45 | 10 | 10 | — | 5 |
| S9 | 50 | — | — | — | 20 | — | — | — | 30 |

(2) Evaluation of Properties

The time for protective shield formation, hemostatic potential and gel strength of the samples are presented in the following Tables 2 and 3. In the Tables 2 and 3, "O" refers to 'suitable' and "X" refers to 'unsuitable'.

TABLE 2

Figure 1:
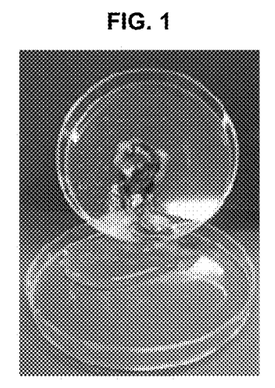
FIG. 1 to FIG. 22 show the photographs obtained by evaluating hemostatic potentials of the powder formulations according to the present invention.
Figure 2:
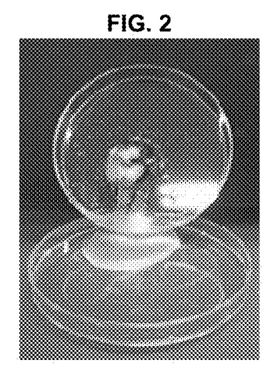
Figure 3:
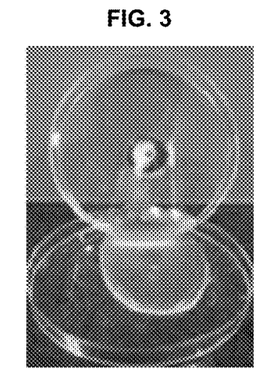
Figure 4:
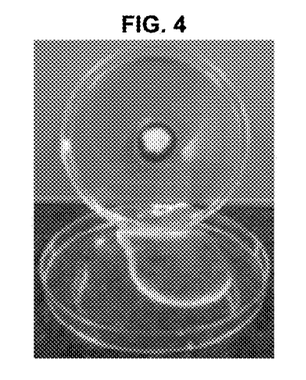
Figure 5:
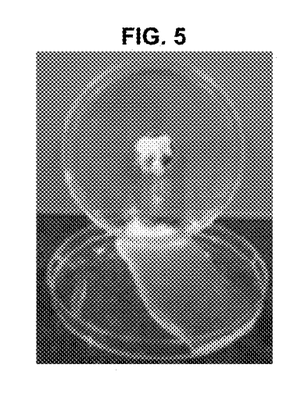
Figure 6:
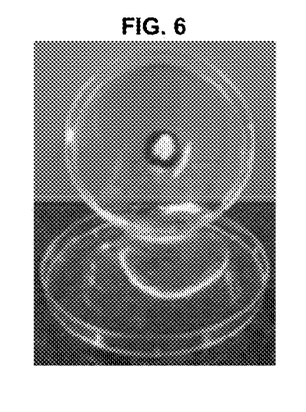
Figure 7:
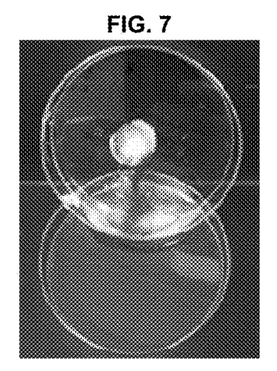
Figure 8:
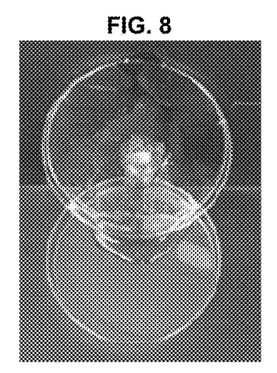
Figure 9:
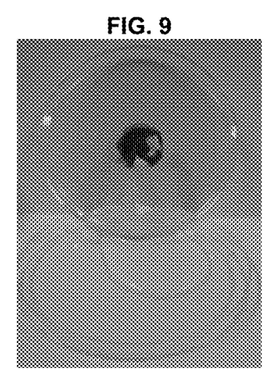

| Sample | Time for protective shield formation | Gel strength Maximum force (N) | Gel strength Tensile strength (MPa = kgf/cm²) | Hemostatic potential Photo-graph | O/X |
|---|---|---|---|---|---|
| S1 | No protective shield formation | 2.4 | 0.19 (X) | FIG. 1 | X |
| S2 | Immediate protective shield formation | 13.93 | 1.11 (O) | FIG. 2 | O |
| S2-1 | Immediate protective shield formation | 7.94 | 0.64 (O) | FIG. 3 | O |
| S2-2 | Immediate protective shield formation | 5.88 | 0.48 (O) | FIG. 4 | O |
| S2-3 | Immediate protective shield formation | 5.1 | 0.41 (O) | FIG. 5 | O |
| S2-4 | Immediate protective shield formation | 4.9 | 0.40 (O) | FIG. 6 | O |
| S2-5 | Immediate protective shield formation | 4.41 | 0.36 (Δ) | FIG. 7 | Δ |
| S2-6 | Immediate protective shield formation | 4.61 | 0.37 (Δ) | FIG. 8 | X |
| S2-7 | Immediate protective shield formation | 7.35 | 0.59 (O) | FIG. 9 | O |

TABLE 3

Figure 10:
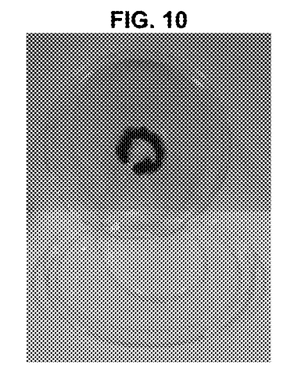
Figure 11:
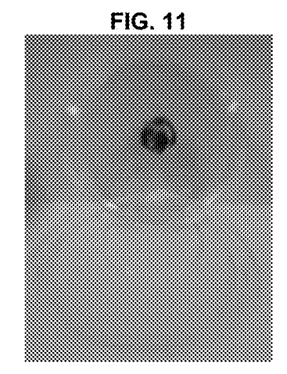
Figure 12:
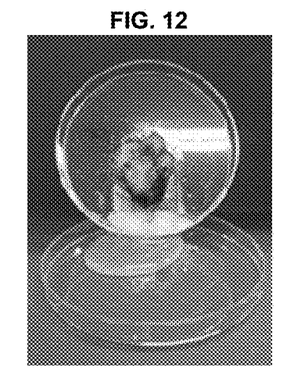
Figure 13:
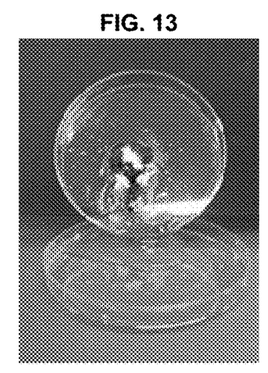
Figure 14:
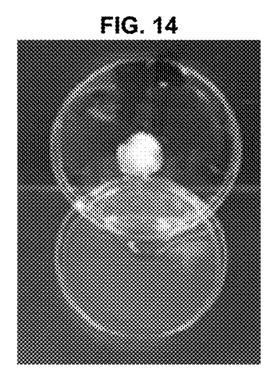
Figure 15:
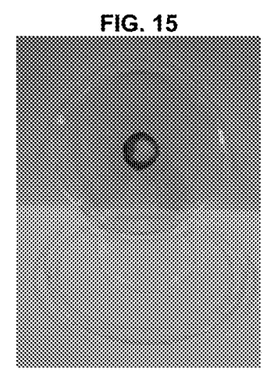
Figure 16:
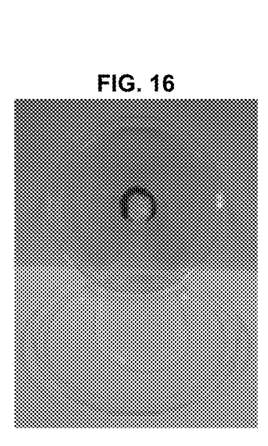
Figure 17:
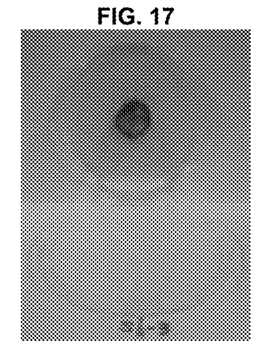
Figure 18:
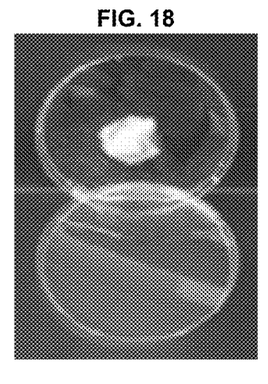
Figure 19:
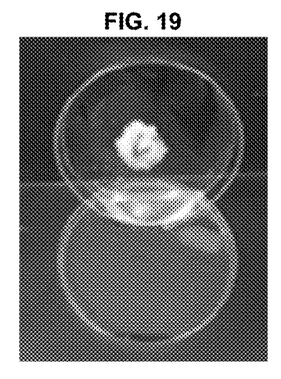
Figure 20:
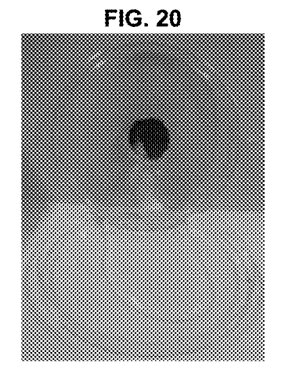
Figure 21:
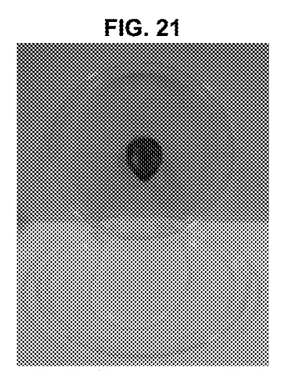
Figure 22:
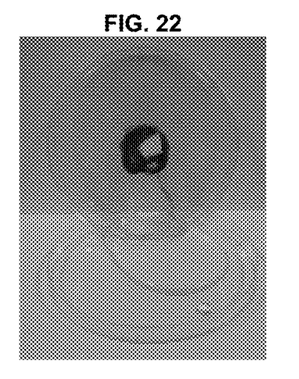

| Sample | Time for protective shield formation | Gel strength Maximum force (N) | Gel strength Tensile strength (MPa = kgf/cm²) | Hemostatic potential Photo-graph | O/X |
|---|---|---|---|---|---|
| S2-8 | Immediate protective shield formation | 5.10 | 0.41 (O) | FIG. 10 | O |
| S3 | 600 seconds | 0.9 | 0.07 (X) | FIG. 11 | O |
| S4 | No protective shield formation | 0.6 | 0.05 (X) | FIG. 12 | X |
| S5 | No protective shield formation | 3.1 | 0.24 (X) | FIG. 13 | X |
| S6 | 60 seconds | 12.41 | 0.99 (O) | FIG. 14 | O |
| S6-1 | 5 seconds | 5.98 | 0.49 (O) | FIG. 15 | O |
| S6-2 | 180 seconds | 1.96 | 0.16 (X) | FIG. 16 | O |
| S6-3 | 150 seconds | 10.01 | 0.78 (O) | FIG. 17 | O |
| S7 | 70 seconds | 6.52 | 0.52 (O) | FIG. 18 | O |
| S8 | 120 seconds | 6.67 | 0.53 (O) | FIG. 19 | O |
| S8-1 | 10 seconds | 5.68 | 0.46 (O) | FIG. 20 | O |
| S8-2 | 120 seconds | 1.57 | 0.13 (X) | FIG. 21 | O |
| S9 | 45 seconds | 1.39 | 0.11 (X) | FIG. 22 | Δ |

(2-1) Hemostatic Potential

Each sample and a blood were reacted at a ratio of 1:1 in a petri dish. After 1 minute of the reaction, excess of water (10 mL) was sprayed thereon for examining whether the hemostatis is maintained. The samples S6 to S9 containing calcium chloride showed good hemostatis. And, the samples S2, S2-1 to S2-4, S2-7, S2-8, and S3, not containing calcium chloride, also showed hemostatis by physical protective shield formed through immediate gel-formation. However, the samples S2-5 and S2-6 did not show hemostatis, which was originated from the lack of chemical hemostatic agent. And also, the samples S1, S4, and S5 did not show hemostatis, which was originated from the lack of physical protective-shield formation.

(2-2) Gel Strength

Each sample was reacted with water at a weight ratio of 1:10 to obtain a gel. The gel strength was determined with a rheometer under the following conditions.

Spindle: No. 25
Maximum load: 20 N
Tensile distance: 5 mm
Crosshead speed: 120.0 mm/min In order to compare the degrees enduring against external stress, the tensile strength of the resulting gels were determined. The tensile strength of each sample was calculated according to the following formula: Tensile strength (MPa)= maximum force (N)/cross-sectional area of the sample (A)

As the results thereof, the sample S2, which had been determined to have the most excellent immediate gel-formation potential, showed the highest tensile strength. The samples S2-1 to S2-4, S2-7, S2-8, S6, S6-1, S6-3, S7, S8, and S8-1 also showed relatively high tensile strengths. The sample S9, which consists of the mucoadhesive polymer and the hemostatic inorganic material without a hygroscopic agent, showed sharply decreased tensile strength. And also, among the samples containing both the mucoadhesive polymer and the hygroscopic agent, the samples containing sodium alginate or chitosan as the mucoadhesive polymer showed almost zero (0) of gel strength.

Example 2: In-Vivo Studies (1) Preparation of Powder Formulation

For in-vivo studies, we used a powder formulation consisting of a mucoadhesive polymer (hydroxyethyl cellulose) and a hygroscopic agent (croscarmellose sodium and sodium starch glycolate), along with epidermal growth factor (EGF) as a wound-healing to agent. The powder formulation was prepared by mixing hydroxyethyl cellulose (899.99 mg), croscarmellose sodium (50 mg), sodium starch glycolate (50 mg), and EGF (10 μg), based on 1 g of the powder formulation. The powder formulation is referred to as "Formulation" in this Example 2.

(2) Methods

<1> Animals

Six female mini-pigs (Micro-pig®; Medi Kinetics, Pyeongtaeck, Korea) weighing 35 to 40 kg, and 46 male rabbits (New Zealand White; Orient Bio, Seongnam, Korea) weighing 2 to 2.5 kg were used for the experiments. All animal care and experimental procedures were conducted in accordance with the guidelines of the Experimental Animal Research Committee of Inha University (Incheon, Korea).

<2> Animal Models for Gastric Hemorrhage

Gastric hemorrhage models were developed against rabbits and mini-pigs in the studies. Rabbit mucosectomy-induced gastric hemorrhage models were developed as follows. Rabbits were fasted for 24 hours prior to the operation, then anesthetized with an intramuscular injection of a mixture of ketamine (4.2 mg/kg) and xylazine (11.7 mg/kg). Rabbits were randomly divided into a non-treated group, an epinephrine-injected group and a Formulation-treated group. The stomach was exposed and surgically opened along the greater curvature. Then, 200 µl of isotonic saline was injected into the submucosal layer of the stomach. The swollen gastric mucosa was resected using a pair of operating scissors. The resected area was around 7-10 mm in diameter. After each treatment, the duration of the bleeding time was measured.

Endoscopic mucosectomy-induced gastric hemorrhage models of mini-pigs were developed as follows. First, mini-pigs were deprived of food for 36 hours before the endoscopy. Anesthesia was induced via an intramuscular injection of the product tiletamine/zolazepam sold under the trademark Zoletil® by Virbac Korea in Seoul, Korea and the product xylazine sold under the trademark Narcoxyl-2® by Intervet Korea Ltd. in Seoul, Korea and maintained with inhalation of the product isoflurane sold under the trademark Ifran® by Hana Pharm. in Gyeonggi-do, Korea during the operation. The endoscope (GIF-Q260; Olympus Medical Systems, Tokyo, Japan) was inserted with the animals in a lateral decubitus position. The target areas were marked with an argon plasma coagulator (APC), and isotonic saline was injected into the submucosal layer. An endoscopic submucosal dissection was performed to produce acute ulcers with diameters of 2.0-3.0 cm in the anterior and posterior walls in the stomach.

<3> Hemostatic and Ulcer-Healing Action of the Formulation

Hemostatic action of the Formulation on gastric muco-resected rabbit models was evaluated. After the laparoscopic resection of the gastric mucosa, the bleeding area was covered with the Formulation, and mean bleeding time was measured and compared with another conventional treatment, i.e., an epinephrine local-injection. In the porcine models, muco-resection was performed via an endoscope and then the bleeding-focus was covered with the Formulation. Instant hemostatic action of the Formulation on acute bleeding and rebleeding after the treatment were observed via an endoscopy for 24 hours. If bleeding continued within three minutes after first application, a second application was performed to the wound according to the first application. After the treatment, the animals were observed for 24-hours.

The ulcer healing effect of the Formulation was mainly observed via the assessment of histology. One day after the treatments, the stomach was recovered and the related ulcer area was calculated as the ulcer area divided by the initial ulcer area. For the porcine models, ulcers were observed via endoscopies. Three days after the treatments, the mini-pigs were sacrificed and tissues were harvested and stained for histological assessment.

<4> Histological Studies

The recovered mucosal tissues were fixed in 4% formalin, embedded in paraffin blocks and then stained with hematoxylin and eosin (H&E) staining using routine procedures. H&E-stained sections were analyzed to assess gastric glandular structures and measure the thickness of the regenerated gastric mucosa at the ulcer site under a microscope.

<5> Statistical Analysis

All data were reported as the mean±SEM. Experimental results were analyzed with a T-test, a One-way ANOVA on ranks followed by Tukey's post-hoc test or a Two-way ANOVA on ranks followed by Bonferroni multiple comparisons using PRISM 5 software. P-values $<0.05$, $<0.01$, $<0.001$, or $<0.0001$ were considered statistically significant.

(3) Results

<1> Hemostatic Function of the Formulation

Figure 23:
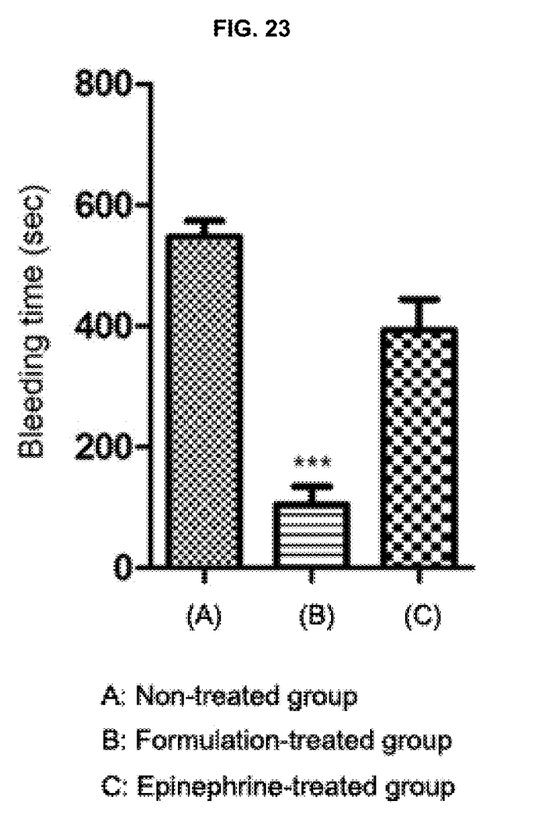
FIG. 23 shows hemostatic action of the powder formulation of the present invention on the mucosal-resection induced gastric bleeding model of rabbits.
Figure 24:
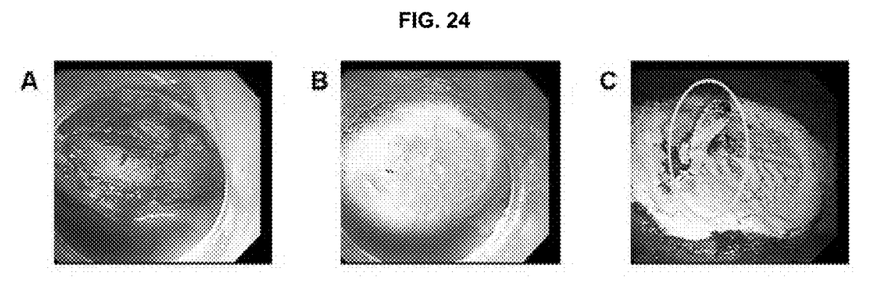
FIG. 24 shows hemostatic action of the powder formulation of the present invention on the endoscopic mucosal-resection induced gastric bleeding model of mini-pigs. A) gastric hemorrhage before treatment, B) endoscopy image of gastric ulcer at 3 minutes after the treatment, and C) endoscopic image of gastric ulcer at 6 minutes after the treatment.

The hemostatic function of the Formulation was observed on gastric mucoresection-induced bleedings of rabbits and mini-pigs. In the rabbit models, the average bleeding time under each treatment is shown in FIG. 23. Non-treated and epinephrine local-injection yielded about 548 seconds and about 393 seconds of bleeding time, respectively. Contrarily, the treatment of the Formulation displayed a significantly shortened bleeding time (104 seconds, $p<0.001$). The Formulation also showed immediate hemostatic function, covering the bleeding focus. Bleeding stopped in 12 minutes to 26 minutes and was secured for 72 hours after the first treatment of the Formulation (FIG. 24). No secondary treatment was required in this study.

<2> Ulcer Healing Activities of the Formulation

Figure 25:
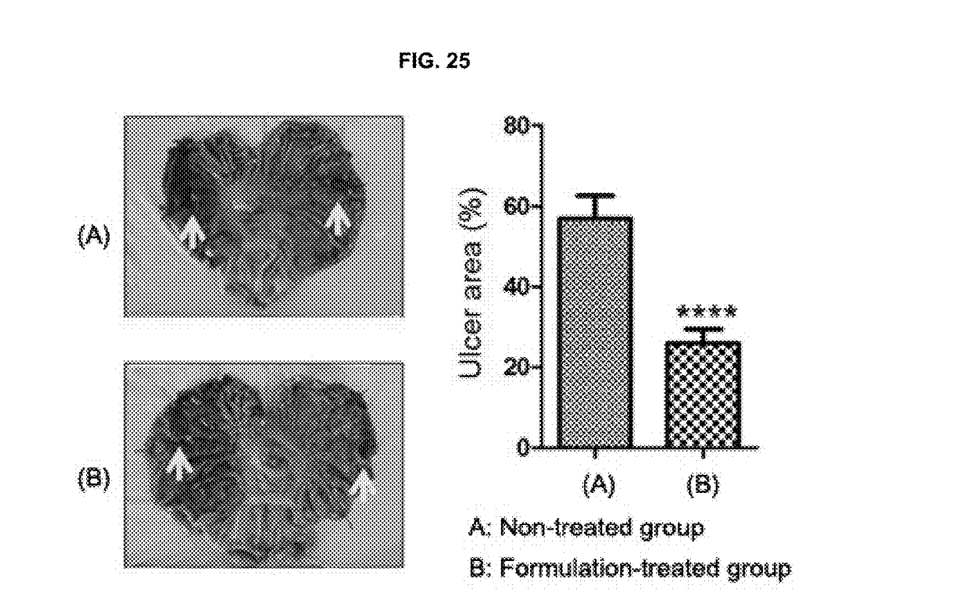
FIG. 25 shows the reduced ulcer area (precipitated ulcer healing) after treatment of the powder formulation of the present invention.
Figure 26:
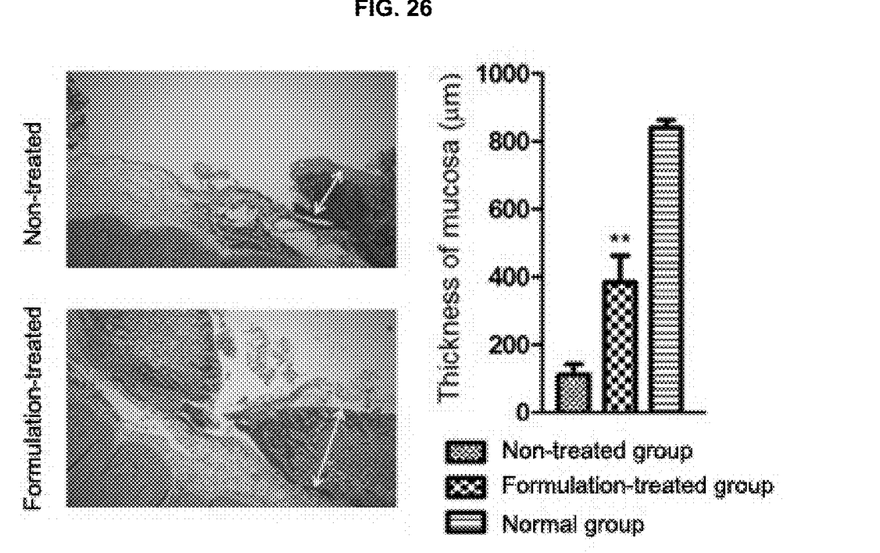
FIG. 26 shows the histological observation of precipitated mucosal healing (thickness) after treatment of the powder formulation of the present invention on rabbit gastric ulcer and hemorrhage models.
Figure 27:
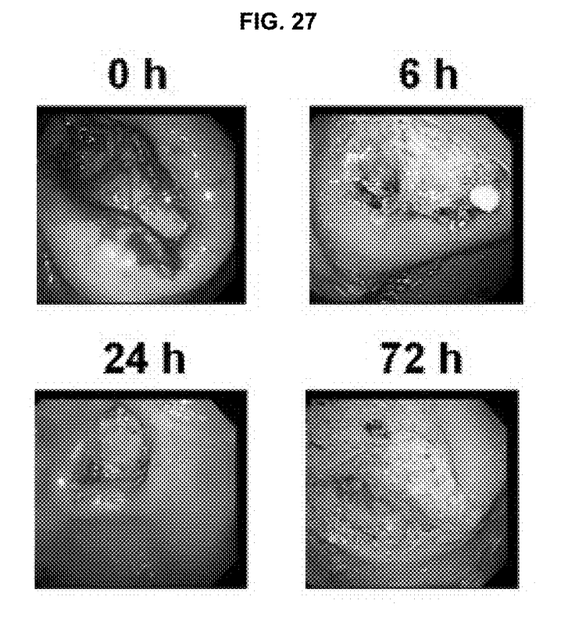
FIG. 27 shows the endoscopic observation of the extended ulcer covering and hemostatic action of the powder formulation of the present invention up to 72 hours of endoscopic-mucoresection gastric hemorrhages on mini-pig models.
Figure 28:
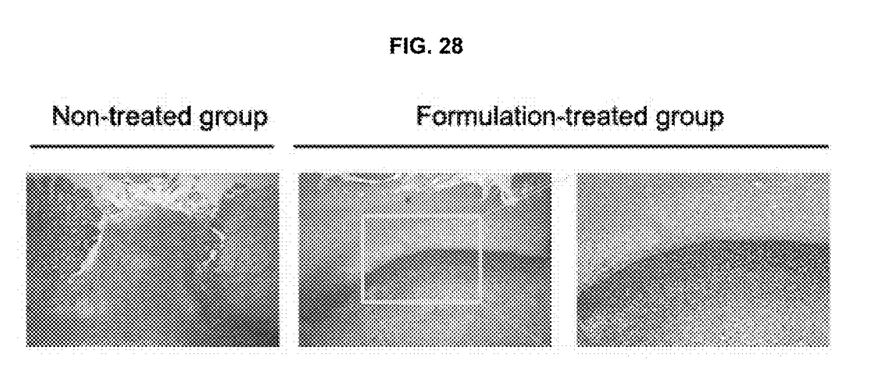
FIG. 28 shows the hematoxylin and eosin (H&E) staining images of control (non-treated) and the powder formulation of the present invention-treated mucosa in mini-pigs.

After allowing 1 day of healing, rabbits were sacrificed with an intramuscular injection of ketamine/xylazine (10/3 mg/kg). Gastric tissues were harvested and further processed for histology. Direction visualization of the gastric mucosa revealed the ulcer healing was precipitated with the Formulation treatment (FIG. 25). The relative ulcer size was significantly reduced in comparison with the non-treated groups (56.8% vs 26.0%, $p<0.00001$). Histology also supported the Formulation precipitated recovery of the gastric mucosa structure. Endoscopic mucosal resection-induced ulcers in the mini-pigs also displayed more enhanced ulcer-healing and rehabilitated mucosa structure by treatment of the Formulation (FIGS. 26 to 28). The Formulation forms a covering hydrogel on the ulcer lesion (FIG. 28).

The invention claimed is:

1. A pharmaceutical composition in a powder form for providing wound protection, hemostasis, or anti-adhesion in the gastrointestinal tract, which consists of:
    a mucoadhesive polymer selected from the group consisting of hydroxyethyl cellulose, polyethylene oxide, and a mixture thereof;
    a hygroscopic agent selected from the group consisting of croscarmellose sodium, sodium starch glycolate, crospovidone, and a mixture thereof, and
    a wound-healing agent selected from the group consisting of epidermal growth factor, keratinocyte growth factor, basic fibroblast growth factor, and a mixture thereof; and
    wherein the mucoadhesive polymer, the hygroscopic agent and the wound-healing agent are present in an amount of 70-95 wt %, 5-30 wt %, and 0-0.01 wt %, respectively, based on the total weight of the composition, and
    wherein the composition is to be administered into the gastrointestinal tract through an endoscope, and
    wherein the pharmaceutical composition forms a physical protective shield at the applied site in the gastrointestinal tract through immediate gel-formation within 150 seconds by reacting the composition with a blood.

2. The pharmaceutical composition according to claim 1, wherein the wound-healing agent is epidermal growth factor.

3. The pharmaceutical composition according to claim 2, consisting of hydroxyethyl cellulose, croscarmellose sodium, and sodium starch glycolate.

4. The pharmaceutical composition according to claim 3, consisting of 90 wt % of hydroxyethyl cellulose, 5 wt % of croscarmellose sodium, and 5 wt % of sodium starch glycolate.

5. The pharmaceutical composition according to claim 3, consisting of 85 wt % of hydroxyethyl cellulose, 7.5 wt % of croscarmellose sodium, and 7.5 wt % of sodium starch glycolate.

6. The pharmaceutical composition according to claim 2, consisting of hydroxyethyl cellulose, croscarmellose sodium, sodium starch glycolate, and epidermal growth factor.

7. The pharmaceutical composition according to claim 6, consisting of 89.99 wt % of hydroxyethyl cellulose, 5 wt % of croscarmellose sodium, 5 wt % of sodium starch glycolate, and 0.01 wt % of epidermal growth factor.

8. The pharmaceutical composition according to claim 2, consisting of hydroxyethyl cellulose and sodium starch glycolate.

9. The pharmaceutical composition according to claim 8, consisting of 90 wt % of hydroxyethyl cellulose and 10 wt % of sodium starch glycolate.

10. A pharmaceutical composition in a powder form for providing wound protection, hemostasis, or anti-adhesion in the gastrointestinal tract, which consists of:
   a mucoadhesive polymer selected from the group consisting of hydroxyethyl cellulose, polyethylene oxide, and a mixture thereof;
   a hygroscopic agent selected from the group consisting of croscarmellose sodium, sodium starch glycolate, crospovidone, and a mixture thereof;
   an inorganic material selected from the group consisting of calcium chloride, calcium phosphate, calcium hydroxide, calcium silicate, calcium sulfate, and a mixture thereof;
   a wound-healing agent selected from the group consisting of epidermal growth factor, keratinocyte growth factor, basic fibroblast growth factor, and a mixture thereof; and
   wherein the mucoadhesive polymer, the hygroscopic agent, the inorganic material, and the wound healing agent are present in an amount of 40-75 wt %, 5-30 wt %, 10-40 wt %, and 0-0.01 wt %, respectively, based on the total weight of the composition, and
   wherein the composition is to be administered into the gastrointestinal tract through an endoscope, and
   wherein the pharmaceutical composition forms a physical protective shield at the applied site in the gastrointestinal tract through immediate gel-formation within 150 seconds by reacting the composition with a blood.

11. The pharmaceutical composition according to claim 10, wherein the mucoadhesive polymer, the hygroscopic agent, and the inorganic material are present in an amount ranging from 50 to 70 wt %, from 10 to 20 wt %, and from 10 to 30 wt %, respectively, based on the total weight of the composition.

12. The pharmaceutical composition according to claim 10, consisting of hydroxyethyl cellulose, polyethylene oxide, sodium starch glycolate, and calcium chloride.

13. The pharmaceutical composition according to claim 12, consisting of 30 wt % of hydroxyethyl cellulose, 20 wt % of polyethylene oxide, 20 wt % of sodium starch glycolate, and 30 wt % of calcium chloride.

* * * * *